US012748089B2

(12) United States Patent
Warner et al.

(10) Patent No.: US 12,748,089 B2
(45) Date of Patent: Sep. 29, 2026

(54) EMI PROTECTED ENCLOSURE WITH INTEGRAL INDICATOR-LIGHT GUIDES FOR GAS DETECTORS

(71) Applicant: Carrier Corporation, Palm Beach Gardens, FL (US)

(72) Inventors: Tanner Warner, Chanhassen, MN (US); Zach Pennaz, Andover, MN (US)

(73) Assignee: DETECTOR ELECTRONICS BUYER US, LLC, Stamford, CT (US)

( * ) Notice: Subject to any disclaimer, the term of this patent is extended or adjusted under 35 U.S.C. 154(b) by 363 days.

(21) Appl. No.: 18/331,401

(22) Filed: Jun. 8, 2023

(65) Prior Publication Data

US 2023/0408469 A1 Dec. 21, 2023

Related U.S. Application Data

(60) Provisional application No. 63/366,023, filed on Jun. 8, 2022.

(51) Int. Cl.
*G01N 33/00* (2006.01)
*H10W 42/20* (2026.01)

(52) U.S. Cl.
CPC ........ *G01N 33/0009* (2013.01); *H10W 42/20* (2026.01)

(58) Field of Classification Search
CPC .............. G01H 33/0009; H01L 23/552; H01L 2924/3025
See application file for complete search history.

(56) References Cited

U.S. PATENT DOCUMENTS 4,814,571 A 3/1989 Bowen et al.
6,071,128 A * 6/2000 Brewington .......... H01L 23/552 257/E23.114
6,307,478 B1 * 10/2001 Thompson ............. G08B 21/14 340/693.5
2003/0224643 A1 12/2003 Starta et al.
2009/0283876 A1 * 11/2009 Behun ..................... H01L 23/10 257/659
2013/0265696 A1 * 10/2013 Smyth ..................... G06F 1/182 361/679.01
2016/0213033 A1 7/2016 Kim et al.
(Continued)

FOREIGN PATENT DOCUMENTS

CN 212904644 U * 4/2021

OTHER PUBLICATIONS

English translation of CN-212904644 accessed from iq.ip.com.*
(Continued)

*Primary Examiner* — Kristina M Deherrera
*Assistant Examiner* — Jean F Morello
(74) *Attorney, Agent, or Firm* — CANTOR COLBURN LLP

(57) ABSTRACT

An enclosure for gas detectors is disclosed. In some embodiments, the enclosure is configured to house a gas sensor. The enclosure comprises a cover configured to be detachably connected to the enclosure. The cover comprises one or more openings configured for providing a Faraday cage; and a top layer configured for covering the one or more openings and guiding an indicator light from inside the enclosure to outside the enclosure.

17 Claims, 3 Drawing Sheets

(56) References Cited

U.S. PATENT DOCUMENTS

| | | | | |
|---|---|---|---|---|
| 2020/0095118 | A1 | 3/2020 | Simbuerger et al. | |
| 2022/0034797 | A1 * | 2/2022 | Bryzgalov | G01N 21/3504 |

OTHER PUBLICATIONS

European Search Report for Application No. 23178237.6, Issued Dec. 18, 2023, 7 Pages.

European Notice of Allowance for Application No. 23178237.6, Issued Sep. 19, 2025, 5 Pages.

* cited by examiner

EMI PROTECTED ENCLOSURE WITH INTEGRAL INDICATOR-LIGHT GUIDES FOR GAS DETECTORS

CROSS REFERENCE TO A RELATED APPLICATION

The application claims the benefit of U.S. Provisional Application No. 63/366,023 filed Jun. 8, 2022, the contents of which are hereby incorporated in their entirety.

BACKGROUND

The invention relates generally to enclosures for gas detectors, more specifically, to electromagnetic interference protected enclosures for gas detectors.

Generally, intrinsically-safe, hazardous location, gas detectors use cemented windows to allow indicator lights to be viewed from outside the device. However, cemented windows may not always be practical.

BRIEF DESCRIPTION

Aspects of the disclosure relate to methods, apparatuses, and/or systems for electromagnetic interference protected enclosures for gas detectors.

An enclosure for a gas detector is disclosed. In some embodiments, the enclosure is configured to house a gas sensor. The enclosure comprises a cover configured to be detachably connected to the enclosure. The cover comprises: one or more openings configured for providing a Faraday cage; and a top layer configured for covering the one or more openings and guiding an indicator light from inside the enclosure to outside the enclosure.

In some embodiments, the top layer is overmolded over a portion of the cover.

In some embodiments, the top layer comprises a transparent material.

In some embodiments, one or more parameters of the openings are determined based on an electromagnetic signal to be blocked by the Faraday cage. The one or more parameters comprise size, shape, and/or distribution of the one or more openings.

In some embodiments, the top layer comprises one or more of polymethyl methacrylate (PMMA), polycarbonate, acrylonitrile butadiene styrene (ABS), high density polyethylene (HDPE), nylon, polyetherimide (PEI), polyethylene terephthalate (PET), polypropylene (PP), and/or polystyrene (PS).

In some embodiments, a method for manufacturing an enclosure for a gas detector comprises providing a housing configured to house a gas sensor; and providing a cover configured to be detachably connected to the housing. The cover comprises one or more openings configured for providing a Faraday cage; and a top layer configured for covering the one or more openings and guiding an indicator light from inside the enclosure to outside the housing.

In some embodiments, a gas detector comprises: a gas sensor and an enclosure. The is configured to house the gas sensor. The enclosure comprises a cover configured to be detachably connected to the enclosure. The cover comprises: one or more openings configured for providing a Faraday cage; and a top layer configured for covering the one or more openings and guiding an indicator light from inside the enclosure to outside the enclosure.

Various other aspects, features, and advantages of the invention will be apparent through the detailed description of the invention and the drawings attached hereto. It is also to be understood that both the foregoing general description and the following detailed description are examples and not restrictive of the scope of the invention.

DETAILED DESCRIPTION

In the following description, for the purposes of explanation, numerous specific details are set forth in order to provide a thorough understanding of the embodiments of the invention. It will be appreciated, however, by those having skill in the art that the embodiments of the invention may be practiced without these specific details or with an equivalent arrangement. In other cases, well-known structures and devices are shown in block diagram form in order to avoid unnecessarily obscuring the embodiments of the invention.

The present disclosure, in accordance with some embodiments, describes an electromagnetic interference (EMI) protected enclosure for gas detectors. Generally, intrinsically-safe gas detectors include electrically conductive material, that is typically opaque, for providing a Faraday cage to prevent EMI. The opaque material doesn't, generally, allow light to travel through it. To overcome this issue, current gas detectors include cemented windows to allow the indicator light to be seen from outside the gas detector. However, the cemented windows may be costly and complicated to manufacture. The EMI protected enclosure as described herein may provide a practical lower cost method to protect the gas sensor while allowing the indicator light to be visible from outside the detector. In some embodiments, a transparent (or relatively transparent) material with high internal reflection may be used to guide the light from the sealed interior of the enclosure to the exterior while maintaining a Faraday cage for EMI protection.

In some embodiments, the gas detector enclosure may include a cover portion configured to operatively attach to the enclosure. The cover may include a conductive portion configured to enclose the sensor electronics and provide a Faraday cage. In some embodiments, the conductive portion may include one or more openings configured to attenuate electromagnetic signals and allow light to go through. In some embodiments, the conductive portion may be overmolded with a transparent material for protecting the sensor and allowing the status indicator lights to be seen on the detector.

Figure 1:
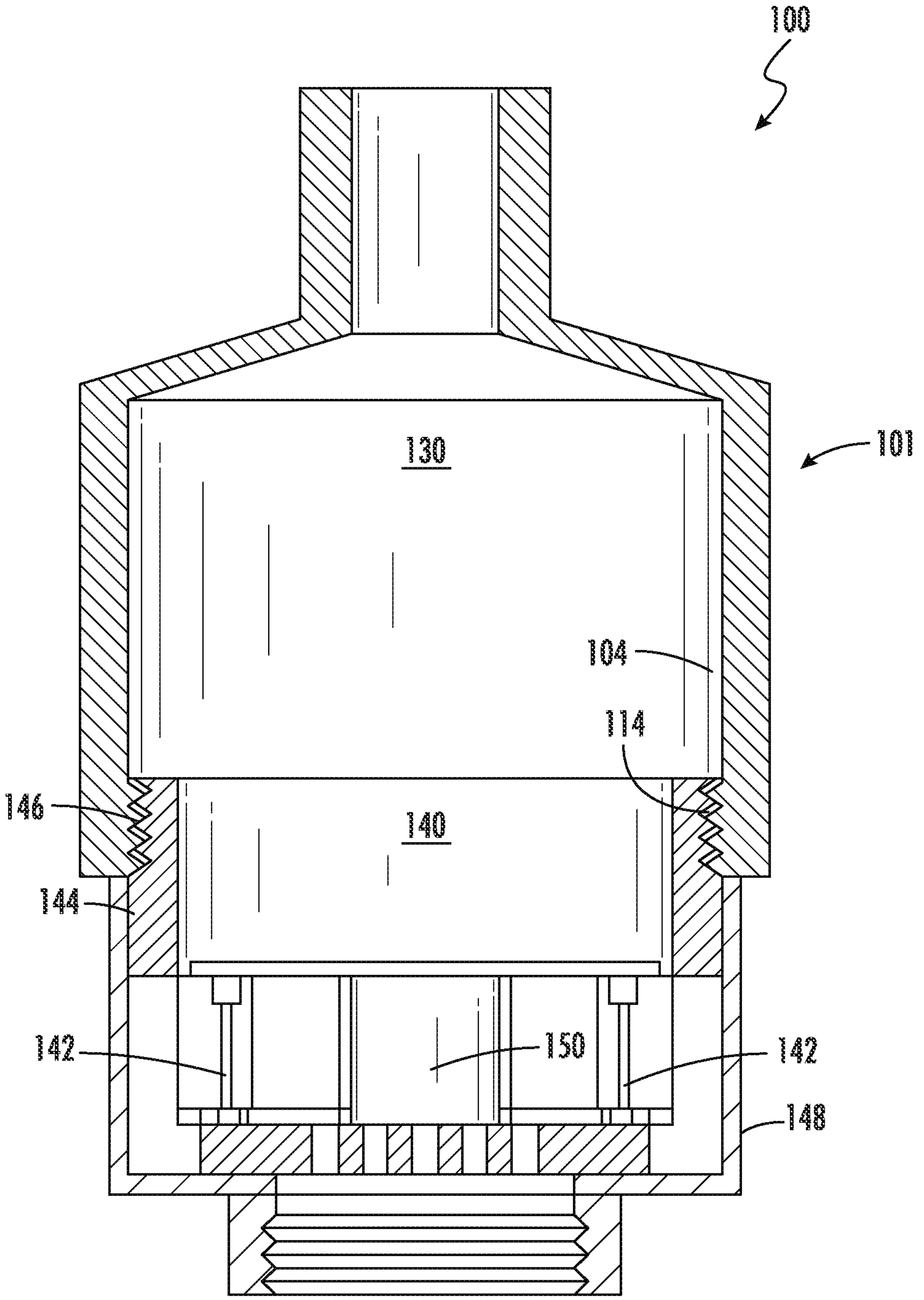
FIG. 1 shows a cross sectional view of an example of a gas detector, in accordance with one or more embodiments.

FIG. 1 is a cross sectional view of an example of a gas detector 100, in accordance with one or more embodiments. In some embodiments, gas detector 100 may include an enclosure 101. In some embodiments, enclosure 101 may include a housing 130 and a cover 140. Enclosure 101 may be configured to house one or more components of gas detector 100. In some embodiments, a gas sensor 150 may be housed within enclosure 101. For example, gas sensor 150 may be detachably connected to enclosure 101 to facilitate removal of gas sensor 150 (e.g., for maintenance, repair, malfunction, or if gas detector 100 is used to detect a different gas). In some embodiments, gas sensor 150 may be an intrinsically safe (IS) gas sensor having intrinsically safe designed control electronics. In some embodiments, gas sensor 150 may include one or more light indicators 154 configured for communicating a status of the sensor (e.g., operational state, fault, alarm, calibration, etc.)

In some embodiments, cover 140 may be configured to be removably connected to housing 130. Cover 140 may house one or more components of gas sensor 150. For example, sensor 150 may be mounted within enclosure 101 such that it fits between housing 130 and cover 140. In some embodiments, cover 140 may include a highly conductive portion configured to attach to housing 130, and to form an electrical path to create a Faraday cage. For example, cover 140 may include threads 146 on outer surface 144 for mating with threads 114 on inner wall 104 of enclosure 101. Other means for connecting cover 140 and housing 130 may be considered and are consistent with the present disclosure.

Figure 2:
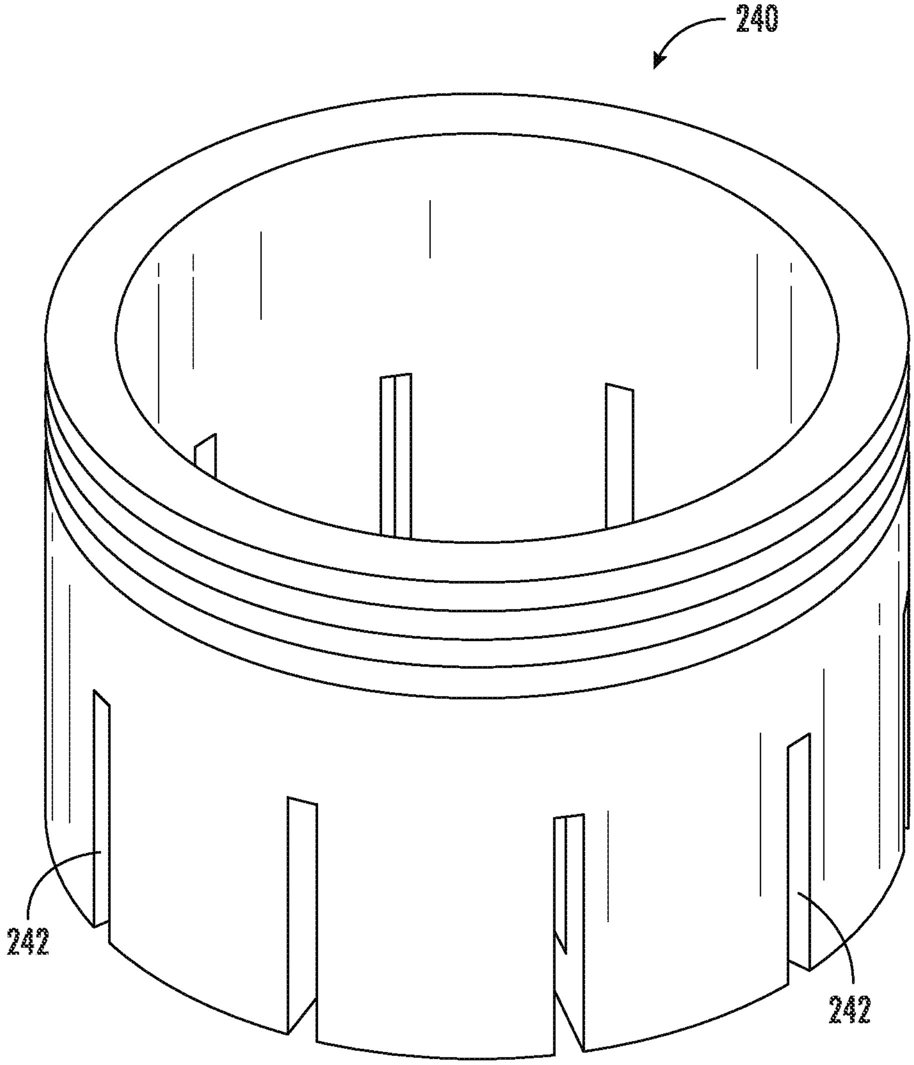
FIG. 2 shows an example of a gas detector cover, in accordance with one or more embodiments.

In some embodiments, the conductive portion of cover 140 may be configured to completely enclose the sensor electronics with a Faraday cage to protect the electronics from outside electromagnetic interference (EMI). The Faraday cage may also block signals inside the detector from radiating to the outside environment. In some embodiments, cover 140 may include one or more openings 142 for providing the Faraday cage. FIG. 2 shows an example of cover 240, according to one or more embodiments. Openings 242 are in the form of slots. However, other shapes, sizes, and distribution may be considered and are compatible with the present disclosure. For example, one or more parameters (size, shape, and/or distribution) of the openings 242 may be chosen based on the electromagnetic signals (e.g., wavelengths) to be blocked while allowing light from the light indicator to pass through.

Figure 3:
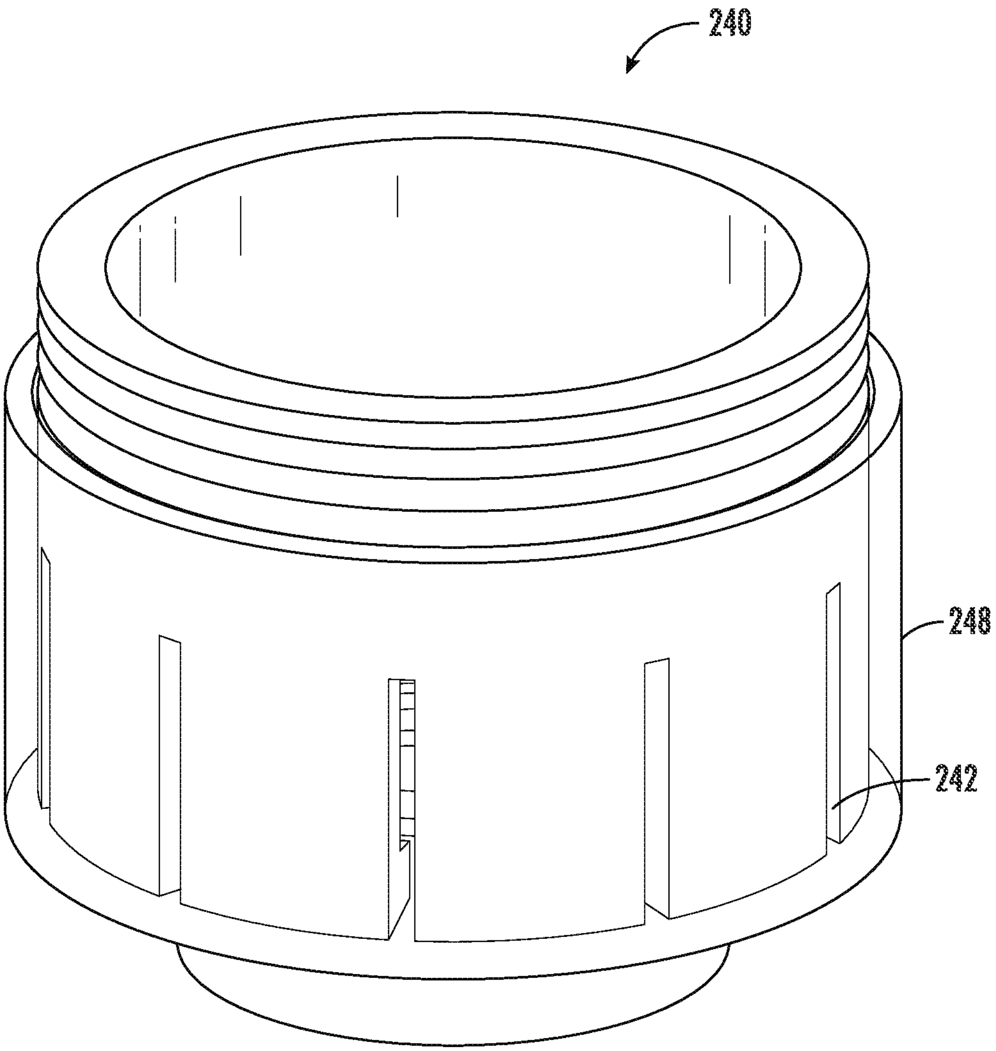
FIG. 3 shows an example of a gas detector cover with a transparent layer, according to one or more embodiments.

Returning to FIG. 1, in some embodiments, a portion of cover 140 may be configured to be covered with a layer of transparent (or relatively transparent) material 148 to protect sensor 150 while allowing status indicator lights to be visible from outside gas detector 100. This may help maintain ingress protection from water and dust while allowing gas to enter the sensor interface in the appropriate area. In some embodiments, the transparent layer may be overmolded over a portion of cover 140 (i.e., injection molding is used to add a layer of the transparent material to cover 140). In some embodiments, the layer of transparent material may be configured to cover the portion of cover 140 that includes openings 142. In some embodiments, layer 148 may be configured to cover the portion of cover 140 below threads 146. In addition to providing a better visual of the light indicators from outside the gas detector, overmolding the transparent layer may also provide time and cost savings. FIG. 3 shows an example of a cover 240 with a transparent layer 248.

In some embodiments, the transparent material used to add a layer to cover 140 may be chosen based on the one or more gas detector parameters (e.g., UV stability, chemical compatibility, thermal expansion and contraction stability, etc.). For example, the transparent material may include one or more of polymethyl methacrylate (PMMA), polycarbonate, acrylonitrile butadiene styrene (ABS), high density polyethylene (HDPE), nylon, polyetherimide (PEI), polyethylene terephthalate (PET), polypropylene (PP), and/or polystyrene (PS).

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

As used throughout this application, the word “may” is used in a permissive sense (i.e., meaning having the potential to), rather than the mandatory sense (i.e., meaning must). The words “include”, “including”, and “includes” and the like mean including, but not limited to. As used throughout this application, the singular forms “a,” “an,” and “the” include plural referents unless the content explicitly indicates otherwise. Thus, for example, reference to “an element” or “a element” includes a combination of two or more elements, notwithstanding use of other terms and phrases for one or more elements, such as “one or more.” The term “or” is, unless indicated otherwise, non-exclusive, i.e., encompassing both “and” and “or.” Terms describing conditional relationships, e.g., “in response to X, Y,” “upon X, Y,”, “if X, Y,” “when X, Y,” and the like, encompass causal relationships in which the antecedent is a necessary causal condition, the antecedent is a sufficient causal condition, or the antecedent is a contributory causal condition of the consequent, e.g., “state X occurs upon condition Y obtaining” is generic to “X occurs solely upon Y” and “X occurs upon Y and Z.” Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Further, unless otherwise indicated, statements that one value or action is “based on” another condition or value encompass both instances in which the condition or value is the sole factor and instances in which the condition or value is one factor among a plurality of factors. Unless otherwise indicated, statements that “each” instance of some collection have some property should not be read to exclude cases where some otherwise identical or similar members of a larger collection do not have the property, i.e., each does not necessarily mean each and every.

What is claimed is:

1. An enclosure for a gas detector, the enclosure configured to house a gas sensor, the enclosure comprising:

a housing;

a cover, the cover configured to be detachably connected to the housing, wherein the cover comprises:

a conductive portion comprising one or more openings, the conductive portion configured for providing a Faraday cage; and a top layer configured for covering the one or more openings and configured for guiding an indicator light from inside the enclosure to outside the enclosure.

2. The enclosure of claim 1, wherein:

the top layer is overmolded over a portion of the cover.

3. The enclosure of claim 2, wherein:

the top layer comprises a transparent material.

4. The enclosure of claim 1, wherein:

the top layer comprises a transparent material.

5. The enclosure of claim 1, wherein:

one or more parameters of the openings are determined based on an electromagnetic signal to be blocked by the Faraday cage, the one or more parameters comprising size, shape, and/or distribution of the one or more openings.

6. The enclosure of claim 1, wherein:

the top layer comprises one or more of polymethyl methacrylate (PMMA), polycarbonate, acrylonitrile butadiene styrene (ABS), high density polyethylene (HDPE), nylon, polyetherimide (PEI), polyethylene terephthalate (PET), polypropylene (PP), and/or polystyrene (PS).

7. A gas detector comprising:

a gas sensor; and the enclosure of claim 1.

8. The gas detector of claim 7, wherein:

the top layer is overmolded over a portion of the cover.

9. The gas detector of claim 7, wherein:

the top layer comprises a transparent material.

10. The gas detector of claim 7, wherein:

one or more parameters of the openings are determined based on an electromagnetic signal to be blocked by the Faraday cage, the one or more parameters comprising size, shape, and/or distribution of the one or more openings.

11. The gas detector of claim 7, wherein:

the top layer comprises one or more of polymethyl methacrylate (PMMA), polycarbonate, acrylonitrile butadiene styrene (ABS), high density polyethylene (HDPE), nylon, polyetherimide (PEI), polyethylene terephthalate (PET), polypropylene (PP), and/or polystyrene (PS).

12. The enclosure of claim 1, wherein the housing comprises first threads on an inner wall of the housing and the cover comprises second threads on an outer surface for mating with the first threads.

13. A method of manufacturing a gas detector, the method comprising:

providing a gas sensor;

providing a housing; and providing a cover, the cover configured to be detachably connected to the housing, wherein the cover comprises:

a conductive portion comprising one or more openings, the conductive portion configured for providing a Faraday cage; and a top layer configured for covering the one or more openings and configured for guiding an indicator light from inside the enclosure to outside the housing.

14. The method of claim 13, further comprising:

overmolding the top layer over a portion of the cover.

15. The method of claim 13, wherein the top layer comprises a transparent material.

16. The method of claim 13, further comprising:

determining one or more parameters of the openings based on an electromagnetic signal to be blocked by the Faraday cage, the one or more parameters comprising size, shape, and/or distribution of the one or more openings.

17. The method of claim 13, wherein:

the top layer comprises one or more of polymethyl methacrylate (PMMA), polycarbonate, acrylonitrile butadiene styrene (ABS), high density polyethylene (HDPE), nylon, polyetherimide (PEI), polyethylene terephthalate (PET), polypropylene (PP), and/or polystyrene (PS).

* * * * *